(12) United States Patent
Tanaka et al.

(10) Patent No.: US 11,702,621 B2
(45) Date of Patent: Jul. 18, 2023

(54) CULTURING CELLS IN A MULTILAYER FILM CONTAINER

(71) Applicant: TOYO SEIKAN GROUP HOLDINGS, LTD., Tokyo (JP)

(72) Inventors: Satoshi Tanaka, Kanagawa (JP); Takahiko Totani, Kanagawa (JP); Yoichi Ishizaki, Kanagawa (JP); Kyohei Ota, Yokohama (JP); Ryo Suenaga, Kanagawa (JP); Masahiro Kuninori, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 0 days.

(21) Appl. No.: 16/232,865

(22) Filed: Dec. 26, 2018

(65) Prior Publication Data
US 2019/0127676 A1    May 2, 2019

Related U.S. Application Data

(63) Continuation of application No. 13/818,862, filed as application No. PCT/JP2011/004964 on Sep. 5, 2011, now abandoned.

(30) Foreign Application Priority Data

Sep. 6, 2010   (JP) ................................. 2010-198708

(51) Int. Cl.
| | |
|---|---|
| *B32B 27/08* | (2006.01) |
| *C12M 1/04* | (2006.01) |
| *B32B 27/32* | (2006.01) |
| *C12M 1/00* | (2006.01) |
| *B32B 7/02* | (2019.01) |
| *B32B 1/02* | (2006.01) |
| *B32B 1/08* | (2006.01) |

(52) U.S. Cl.
CPC ............... *C12M 23/24* (2013.01); *B32B 1/02* (2013.01); *B32B 1/08* (2013.01); *B32B 7/02* (2013.01); *B32B 27/08* (2013.01); *B32B 27/32* (2013.01); *C12M 23/14* (2013.01); *C12M 23/20* (2013.01); *B32B 2250/02* (2013.01); *B32B 2250/03* (2013.01); *B32B 2250/242* (2013.01); *B32B 2307/31* (2013.01); *B32B 2307/412* (2013.01); *B32B 2307/72* (2013.01); *B32B 2307/724* (2013.01); *B32B 2307/732* (2013.01); *B32B 2323/046* (2013.01); *B32B 2439/40* (2013.01); *Y10T 428/2495* (2015.01); *Y10T 428/24992* (2015.01)

(58) Field of Classification Search
CPC ............ B32B 2250/03; B32B 2439/40; B32B 2323/04; B32B 2323/046; B32B 2307/724; B32B 27/08; B32B 7/02; C12M 23/14
See application file for complete search history.

(56) References Cited

U.S. PATENT DOCUMENTS

| | | | | |
|---|---|---|---|---|
| 4,396,582 A | * | 8/1983 | Kodera | ..................... A61L 2/10 422/24 |
| 2003/0213938 A1 | * | 11/2003 | Farley | ................. C08L 23/0815 252/500 |
| 2006/0177641 A1 | * | 8/2006 | Breese | .................. B29C 55/023 428/220 |
| 2009/0191392 A1 | * | 7/2009 | Gkinosatis | .............. B32B 27/08 428/219 |

FOREIGN PATENT DOCUMENTS

| | | | | |
|---|---|---|---|---|
| CN | 102189732 A | * | 9/2011 | |
| EP | 2027999 A1 | * | 2/2009 | ............. B32B 27/08 |

OTHER PUBLICATIONS

Okonkowski et al. Cholesterol Delivery to NS0 Cells: Challengesand Solutions in Disposable Linear Low-Density Polyethylene-Based Bioreactors; Journal of Bioscience and Bioengineering, vol. 103, No. 1, pp. 50-59. (Year: 2007).*

Huang et al. Predicting the Permeability and Tensile Properties of Multilayer Films From the Properties of the Individual Component Layers; Polymer Journal, vol. 36, No. 5, pp. 386-393. (Year: 2004).*

Xiu et al. Estimation of Rates of Oxygen Uptake and Carbon Dioxide Evolution of Animal Cell Culture Using Material and Energy Balances; Cytotechnology, vol. 29, pp. 159-166. (Year: 1999).*

* cited by examiner

*Primary Examiner* — Melissa L Fisher
*Assistant Examiner* — Paul C Martin
(74) *Attorney, Agent, or Firm* — Osha Bergman Watanabe & Burton LLP (57) ABSTRACT

Provided are a multilayer film having excellent gas permeability and excellent handling properties and hence is suited for forming a cell culture container, and a cell culture container formed by using the same.

A multilayer film used for forming a cell culture container, comprising: a base material composed of a polyethylene-based resin having a density of 0.87 g/cm³ to 0.90 g/cm³; and an inner layer composed of a polyethylene-based resin having a density of 0.896 g/cm³ to 0.93 g/cm³ and forming a cell culture icy surface. A cell culture container is formed by using this multilayer film.

7 Claims, 7 Drawing Sheets

CULTURING CELLS IN A MULTILAYER FILM CONTAINER

TECHNICAL FIELD

The present invention relates to a cell culture technology, in particular, relates to a multilayer film having excellent gas permeability and a cell culture container.

BACKGROUND ART

In recent years, in the field of production of medical supplies, gene therapy, regenerative therapy, immune cell therapy or the like, a large amount of a cell, a tissue, a microorganism or the like are required to be cultured effectively in an artificial environment. A dish or a flask which is commonly used for cell culture is not suited to the culture of a large amount of cells. Under such circumstances, a culture bag is used as a culture container for the culture of a large amount of cells. A culture bag is preferable not only since it enables a large amount of cells to be cultured but also it can reduce the risk of contamination by a fungi or virus due to its closed system.

As the conditions required for a resin film constituting a culture bag, gas permeability, transparency, low cytotoxicity, low dissolution behavior, suitability to radiation sterilization or the like can be given.

As the material satisfying these conditions, a polyethylene-based resin is preferable. As the polyethylene-based resin, polyethylene, a copolymer of ethylene and an a-olefin, a copolymer of ethylene and vinyl acetate, an ionomer using a copolymer of ethylene and an acrylic acid or methacrylic acid and a metal ion can be given.

Therefore, conventionally, as a culture bag, a bag formed of a film of LLDPE (linear low-density polyethylene), LDPE (low-density polyethylene), EVA (ethylene-vinyl acetate copolymer resin), an ionomer resin or the like was used since they have the above-mentioned properties and are excellent in molding process ability.

Gas permeability of a conventional culture bag was, however, not sufficient. As compared with an open culture container such as a dish, a conventional culture bag cannot attain a high degree of cell density.

As the example of a cell culture bag using a polyethylene resin, one disclosed in Patent Document 1 can be given, for example. The cell culture bag disclosed in Patent Document 1 is formed of a film comprising 70 to 95 wt % of icy linear low-density polyethylene composed of a copolymer of ethylene and an α-olefin having 6 to 8 carbon atoms and 30 to 5 wt % of low-density polyethylene.

Patent Document 2 discloses a flexible, gas permeable multilayer film which is suited for the formation of a cell culture container composed of a first layer of polystyrene having a thickness of 0.0001 inches to about 0.0010 inches and a second layer composed of a polymer material and is adhered to the first layer and having a thickness of 0.004 inches to about 0.025 inches, or a multilayer gas permeable container using the same.

Patent Document 1: Japanese Patent No. 2643003
Patent Document 2: JP-T-H10-507363

SUMMARY OF THE INVENTION

Problems to be Solved by the Invention

The cell culture bag disclosed in Patent Document 1 is formed of a single layer film formed of a blend of linear low-density polyethylene and low-density polyethylene. The density thereof is not clear, and the thickness of the film is 50 to 300 μm, for example. In general, gas permeability of a polyethylene-based resin is improved by decreasing the degree of crystallization, i.e. the density. However, if the density is lowered above a certain degree, adhesiveness of a resin is increased, whereby handling properties are deteriorated or blocking resistance is lowered. Further, if the thickness of a film is decreased, while the gas permeability of a cell culture container is increased, the strength thereof is decreased. By the single layer film of Patent Document 1, it is impossible to realize a culture bag having high gas permeability and excellent handling properties.

The film disclosed in Patent Document 2 is a multilayer film for forming a cell culture container. However, polystyrene is used in the inner layer which forms a cell culture surface and a polymer material formed of a styrene-ethylene-butadiene-styrene block copolymer, ethylene vinyl acetate and polypropylene or the like is used in the base material. However, by such a configuration, it is impossible to realize satisfactory gas permeability.

The inventors of the present invention made intensive studies. As a result, by using as a base material a very low-density polyethylene having a high gas permeability while it tends to be subjected to blocking easily and is eluted in a large amount, and by using as a cell culture surface a polyethylene-based resin which hardly suffers from blocking and can suppress elution from the base material, the inventors of the present invention successfully developed a multilayer film for use in a cell culture container having excellent gas permeability, blocking resistance, low dissolution behavior and suitability to radiation sterilization. The present invention has been made based on this finding.

That is, the present invention is aimed at providing a multilayer film for a cell culture container having excellent gas permeability, handling properties, blocking resistance, low dissolution behavior and suitability to radiation sterilization, as well as a cell culture container using the same.

Means for Solving the Problem

In order to attain the above-mentioned object, the present invention provides a multilayer film for forming a cell culture container, comprising a base material composed of a polyethylene-based resin having a density of 0.87 g/cm$^3$ to 0.90 g/cm$^3$ and an inner layer composed of a polyethylene-based resin having a density of 0.896 g/cm$^3$ to 0.93 g/cm$^3$ and forming a cell culture surface Further, it is preferable to allow the multilayer film of the present invention to be a multilayer film having at least three layers and having an outer layer composed of a polyethylene-based resin having a density of 0.886 g/cm$^3$ to 0.93 g/cm$^3$.

The cell culture container of the present invention is formed by such a multilayer film.

Advantageous Effects of the Invention

According to the present invention, gas permeability of the cell culture container can be improved without deteriorating the handling properties of the cell culture container. Therefore, culture can be conducted by a container formed of a film having a higher density than that of a conventional culture container, whereby cell proliferation efficiency can be improved.

MODE FOR CARRYING OUT THE INVENTION

Hereinbelow, the embodiments of the present invention will be explained.

First embodiment

Figure 1:
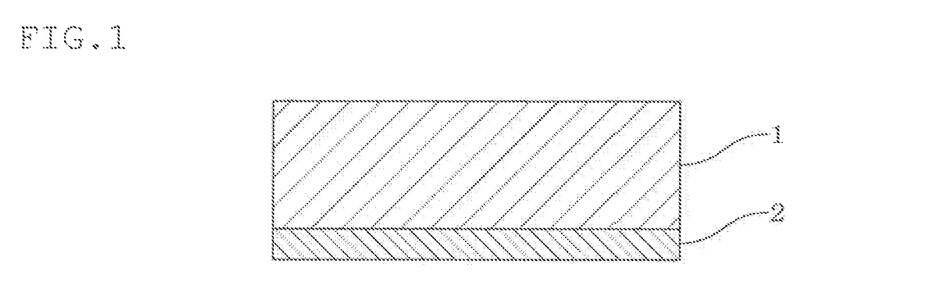
FIG. 1 is a view showing the configuration of a multilayer film according to a first embodiment of the present invention.
Figure 2:
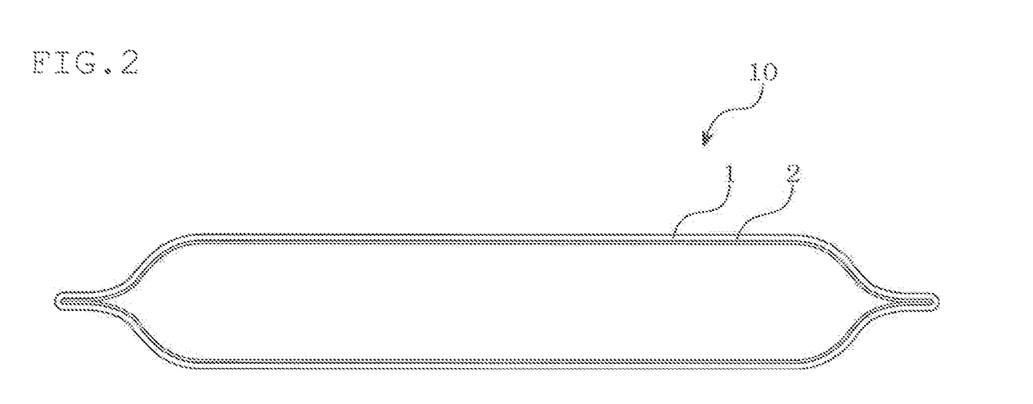
FIG. 2 is a view showing the configuration of a cell culture container formed by the multilayer film according to the first embodiment of the present invention.

The multilayer film and the cell culture container according to the first embodiment of the present invention will be explained with reference to FIG. 1 and FIG. 2. FIG. 1 is a view showing the configuration of the multilayer film of this embodiment, and FIG. 2 is a view showing the configuration of a cell culture container formed by the multilayer film of this embodiment.

As shown in FIG. 1, the multilayer film of this embodiment is used for forming a cell culture container, and has a base material 1 forming the main body part of the cell culture container and an inner layer 2 (innermost layer) forming the cell culture surface.

The base material 1 and the inner layer 2 are formed of a material having a high gas permeability, heat sealing properties and transparency. The inner layer 2 is formed of a material having a low cytotoxicity in addition to the above-mentioned properties. As examples of such a material, a polyethylene-based resin such as linear low density polyethylene (LLDPE), very low density polyethylene (VLDPE)/ultra low density polyethylene (ULDPE), low density polyethylene (LDPE) or a blend thereof can be used.

For the base material 1, it is preferable to use a polyethylene-based resin having a density of 0.87 $g/cm^3$ to 0.90 $g/cm^3$. By using a resin having such a low density as the material forming the main body part of a cell culture container, it is possible to allow the gas permeability of the multilayer film of this embodiment to be excellent.

The density 0.87 $g/cm^3$ to 0.90 $g/cm^3$ of the above-mentioned polyethylene-based resin is the lowest density range which enables handling when this polyethylene-based resin is used as the base material of the multilayer film constituting the cell culture container. That is, if the density is lower than 0.87 $g/cm^3$, it becomes difficult to constitute the film itself due to lowering in softening temperature or melting point. Therefore, it is preferred that the density be 0.87 $g/cm^3$ or more. Further, if the density becomes greater than 0.90 $g/cm^3$, while strength or handling properties are improved, gas permeability is lowered as the density increases. Therefore, it is preferred that the density of the base material be 0.90 $g/cm^3$ or less.

In order to further improve gas permeability, therefore, it is preferred that the density of the base material be 0.885 $g/cm^3$ or less. By allowing the density of the base material of the polyethylene-based resin to be 0.885 $g/cm^3$ or less, the resin has large adhesiveness. If such polyethylene-based resin is used in the cell culture surface, blocking occurs, and as a result, inner surfaces are adhered with each other and are not separated. As a result, it cannot be used as a cell culture container. When the resin is used on the outer surface of the cell culture container, it can be used as the cell culture container although the film itself has adhesiveness.

Therefore, by allowing the multilayer film of the invention to be formed of a base material 1 which forms the main body of the cell culture container and an inner layer 2 which forms the cell culture surface, and by using the resin having a very low density as the base material 1, it is possible to obtain a cell culture container having a high gas permeability and excellent handling properties.

The inner layer 2 constitutes a layer forming the cell culture surface of a cell culture container when a cell culture container is produced by using the multilayer film of this embodiment.

For the inner layer 2, it is preferable to use the above-mentioned polyethylene-based resin having a density of 0.896 $g/cm^3$ to 0.93 $g/cm^3$.

As the material of the inner layer 2 forming the cell culture surface, when the polyethylene-based resin having a density of less than 0.896 $g/cm^3$ is used, blocking occurs, and the inner surfaces are adhered with each other and do not separate from each other, and as a result, it cannot be used as the cell culture container. On the other hand, if the density of the inner layer 2 is 0.896 $g/cm^3$ or more, blocking tends to occur relatively less frequently. Therefore, it is preferred that the density of the inner layer 2 be 0.896 $g/cm^3$ or more.

Further, by allowing the density of the inner layer 2 to be greater than 0.93 $g/cm^3$, the effect of attaining high gas permeability is largely decreased by the inner layer 2. Therefore, it is preferred that the density of the inner layer 2 be 0.93 $g/cm^3$ or less.

It is preferred that the inner layer 2 of this embodiment be one which is produced by not incorporating into the above-mentioned polyethylene-based resin an anti-blocking agent, and/or a supping agent, and/or a lubricant. By incorporating the above-mentioned agents, while blocking hardly occurs in the inner layer 2, proliferation of cells may be inhibited by an anti-blocking agent, and/or a slipping agent, and/or a lubricant, which are eluted. In general, as the anti-blocking agent, the slipping agent or the lubricant, an aliphatic amide or an aliphatic ester, fine particles or the like are used.

In this embodiment, other layers may be formed between the base material 1 and the inner layer 2.

It is preferred that the multilayer film of this embodiment have a configuration in which the thickness of the base material 1 is 1.5 times or more of the thickness of the inner layer 2. That is, the multilayer film of this embodiment has a multilayer structure provided with a base material and an inner layer, In such a structure, if the thickness of the base material 1 is larger than the thickness of the multilayer film by 60% or more, it becomes possible to prevent effects of improving gas permeability from being lowered greatly due to the presence of the inner layer 2 by forming the base material 1 with a polyethylene-based resin having a very low density.

Further, it is preferred that the thickness of the multilayer film of this embodiment be 150 μm or less.

When gas permeability of the cell culture container formed by using the multilayer film is taken into consideration, the thickness of the multilayer film is appropriately 150 μm or less. The same applies to the second embodiment given below.

Due to the above-mentioned configuration, the multilayer film of this embodiment has an oxygen permeability of 750 ml·mm/m$^2$·day·atm (37° C.-80% RH) or more and a carbon dioxide permeability of 2100 ml·mm/m$^2$·day·atm (37° C.-80% RH) or more.

An example of the cell culture container 10 produced by using a multilayer film formed of the base material 1 and the inner layer 2 is shown in FIG. 2. As shown in this figure, in the cell culture container 10, the inner layer 2 is adhered to the inside of the base material 1 formed of a polyethylene-based resin having a very low density, and the inner layer 2 forms the cell culture surface. For this reason, as the material of the base material 1, in respect of blocking as mentioned above, a polyethylene-based resin having a density which is too low to be used as the cell culture surface is used, whereby the gas permeability of the cell culture container is improved. At the same time, by forming the cell culture surface by the inner layer 2, the inner surfaces of the cell culture container can be prevented from being adhered with each other by blocking without being separated and elution from the base material 1 can be suppressed.

Since the multilayer film of this embodiment is formed only of a icy polyethylene-based resin, it has excellent suitability to radiation sterilization which is required for a culture container. As the general sterilization method, sterilization by radiation such as γ rays or electron beam and high-pressure steam sterilization or ethylene oxide gas sterilization or the like can be given. High-pressure steam sterilization takes time, labor or the like. Residual ethylene oxide gas in a product is problematic due to its toxicity. Therefore, it is preferable to conduct sterilization by radiation such as γ rays and electron beam. It cannot apply such a sterilization method to a resin which does not have resistance to radiation. The multilayer film of this embodiment is formed only of a polyethylene-based resin which is improved in resistance to radiation, and hence, can be subjected to sterilization by radiation such as γ rays or electron beam.

As mentioned above, according to the multi-layer film and the cell culture container of this embodiment, as the base material of the cell culture container, a polyethylene-based resin having the lowest possible density range that enables handling can be used, and as the inner layer, a polyethylene-based resin which causes blocking to occur less frequently and has a low density can be used. Therefore, it has suitability to radiation sterilization as the cell culture container. Accordingly, it is possible to provide a cell culture container which has excellent gas permeability and can improve cell culture efficiency as compared with conventional cell culture containers.

Second Embodiment

Figure 3:
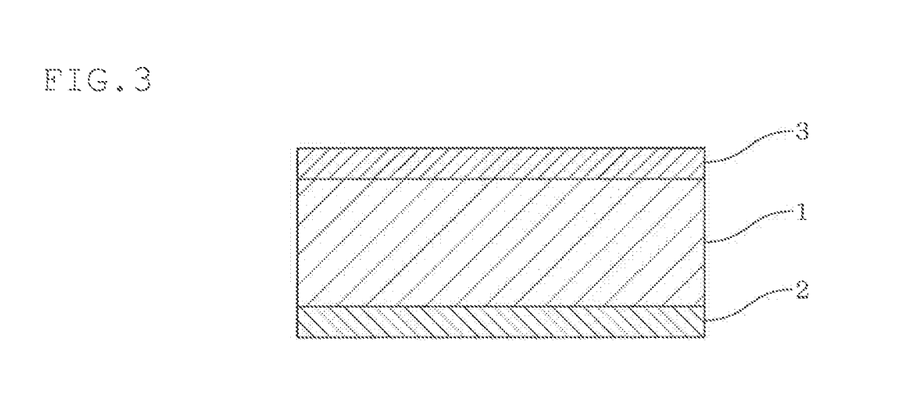
FIG. 3 is a view showing the configuration of a multilayer film according to a second embodiment of the present invention.
Figure 4:
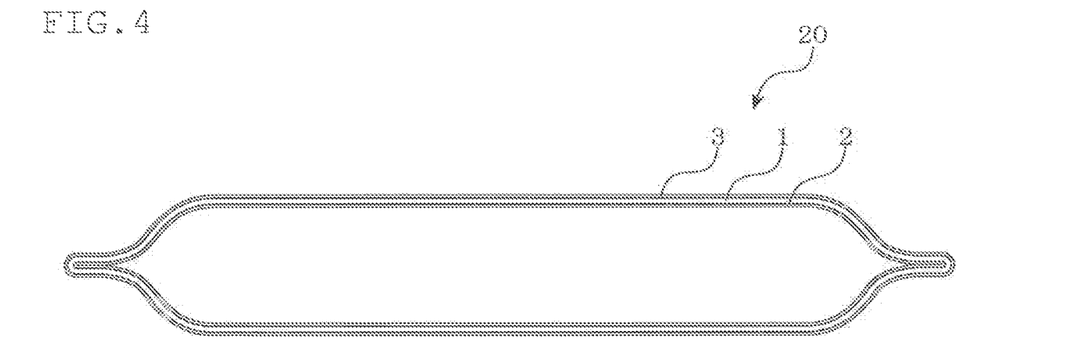
FIG. 4 is a view showing the configuration of a cell culture container formed by the multilayer film according to the second embodiment of the present invention.

Then, the multilayer film and the cell culture container according to the second embodiment of the present invention will be explained with reference to the drawings. FIG. 3 is a view showing the configuration of the multilayer film of this embodiment, and FIG. 4 is a view showing the configuration of the cell culture container formed by the multilayer film of this embodiment.

In this embodiment, the multilayer film has a configuration in which a polyethylene-based resin having a density of 0.886 g/cm$^3$ to 0.93 g/cm$^3$ is used as an outer layer 3 in the first embodiment. In the multilayer film of this embodiment, one or two or more outer layers may be provided between the base material 1 and the outer layer 3. Further, between the base material 1 and the inner layer 2, one or two or more inner layers may be provided.

If the density of the outer layer 3 is smaller than 0.886 g/cm$^3$, production and handling of a cell culture container using the multilayer film may become mechanically difficult. If the density is 0.886 g/cm$^3$ or more, production and handling of a cell culture container become mechanically possible. Therefore, it is preferred that the density of the outer layer 3 be 0.886 g/cm$^3$ or more.

If the density of the outer layer 3 is larger than 0.93 g/cm$^3$, the effect of high gas permeability obtained by using a material having a very low density as the material of the base material 1 is decreased by the outer layer 3. Therefore, it is preferred that the density of the other layer 3 be 0.93 g/cm$^3$ or less.

In the multilayer film of this embodiment, it is preferred that the thickness of the base material 1 be larger by 1.5 times relative to the thickness excluding the base material 1, i.e. the total of the inner layer 2 and the outer layer 3. By allowing the thickness of the base material 1 to be 60% or more in the multilayer film, as mentioned in the first embodiment, a cell culture container can be produced without impairing the effect of improving the gas permeability by the base material 1 by the presence of other layers.

Next, an example of a cell culture container 20 produced by using the multilayer film formed of the base material 1, the inner layer 2 and the outer layer 3 is shown in FIG. 4. As shown in this figure, on the inner surface of the base material 1 which is formed of a polyethylene-based resin having a very low density, the inner layer 2 is adhered to form a cell culture surface. On the outer surface of the base material 1, the outer layer 3 is adhered to form an outer surface of a cell culture container.

In this embodiment, if a polyethylene-based resin having a very low density is used as the material of the base material 1 in order to improve the gas permeability of a cell culture container, the inner layers of the cell culture container do not adhered to each other without being separated. In addition, mechanical handling is possible when a cell culture container is produced.

In this way, the cell culture container of this embodiment has excellent gas permeability in the usage including the production steps without deteriorating handling properties.

As mentioned hereinabove, according to the multilayer film and the cell culture container of this embodiment, as the base material of the film, a icy polyethylene-based resin having the lowest possible density which enables handling can be used, and, as the innermost layer and the outermost layer of the film, a polyethylene-based film which hardly tends to suffer blocking and has a low density can be used.

As a result, a cell culture container which has excellent gas permeability and is easy to handle as compared with conventional cell culture containers can be obtained.

EXAMPLES

Hereinbelow, the examples and the comparative examples regarding the gas permeability test of the multilayer film of the present invention and the examples and the comparative examples regarding the cell culture test of the cell culture container of the present invention will be explained. In the following description, the multilayer film of the present invention may be referred to as the cell culture film and the cell culture container produced by using this film may be referred to as the culture bag.

<Gas Permeation Test>

Example 1

A cell culture film formed of three layers was subjected to co-extrusion molding by the T-die method by using a labo plastomill (manufactured by Toyo Seiki Co., Ltd.). At this time, as the base material, Kernel KS240T (LLDPE, manufactured by Japan Polyethylene Corporation, density, 0.880 g/cm$^3$) was used. As the inner layer and the outer layer, a resin obtained by blending EXCELLEN™ GMHCB 2001 (LDPE, manufactured by Sumitomo Chemical Corporation, density, 0.920 g/cm$^3$) and Kernel KM 262 (LLDPE, manufactured by Japan Polyethylene Corporation, density, 0.898 g/cm$^3$) at an amount ratio of 6:4 was used. In the cell culture film thus produced, the thickness of the base material was 66 μm, the thickness of the inner layer was 19 μm, the thickness of the outer layer was 12 μm, and the total thickness of the cell culture film was 97 μm.

Figure 5:
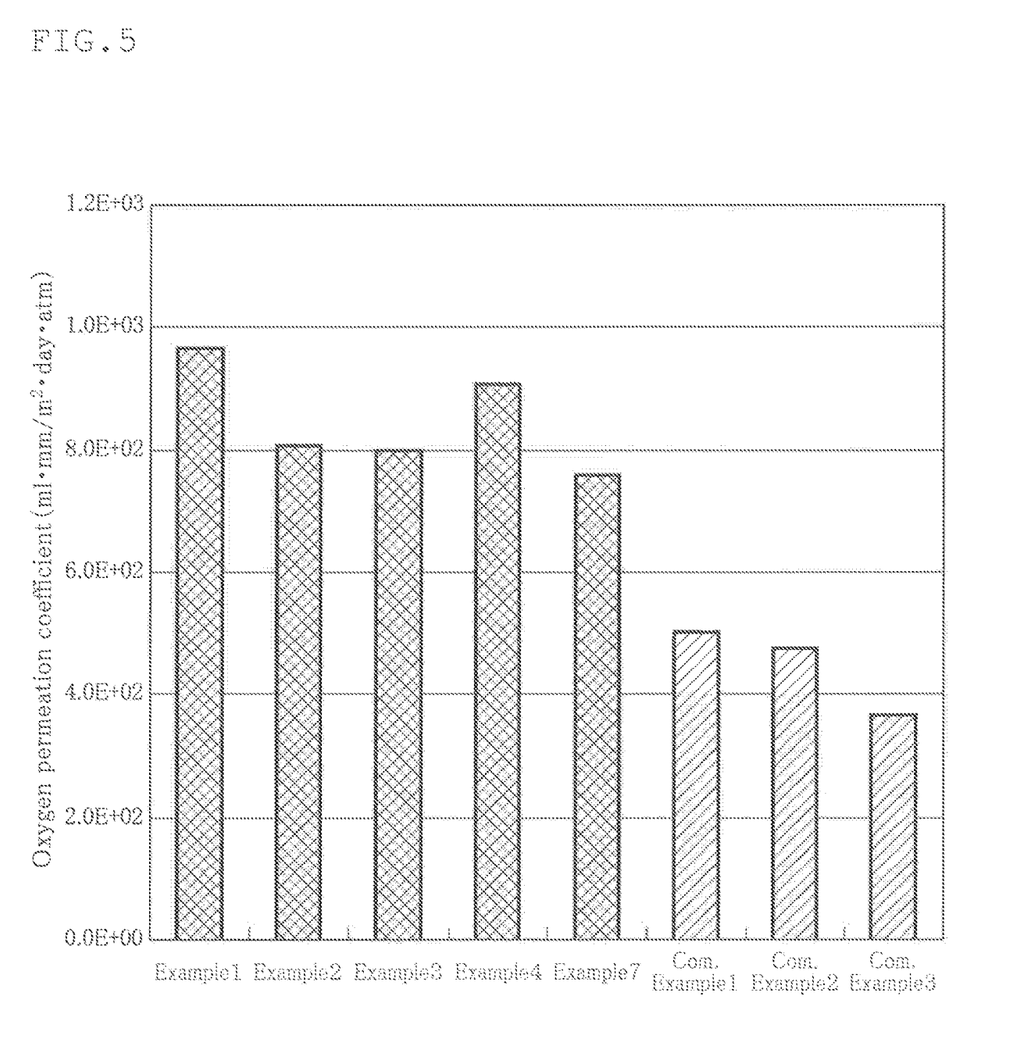
FIG. 5 is a view showing the results of measuring oxygen permeation of the films of Examples and Comparative Examples.

By using this cell culture film, the oxygen permeability per unit thickness (ml·mm/m$^2$·day·atm (37° C.-80% RH)) was measured by means of a gas permeability measuring device GPM-250 (manufactured by GL Science Inc). The results are shown in FIG. 5. This figure shows that, a higher oxygen permeability, a higher gas permeability of the cell culture film.

As shown in the figure, the oxygen permeability of the cell culture film obtained in Example 1 was about 970 ml·mm/m$^2$·day·atm (37° C.-80% RH).

Figure 6:
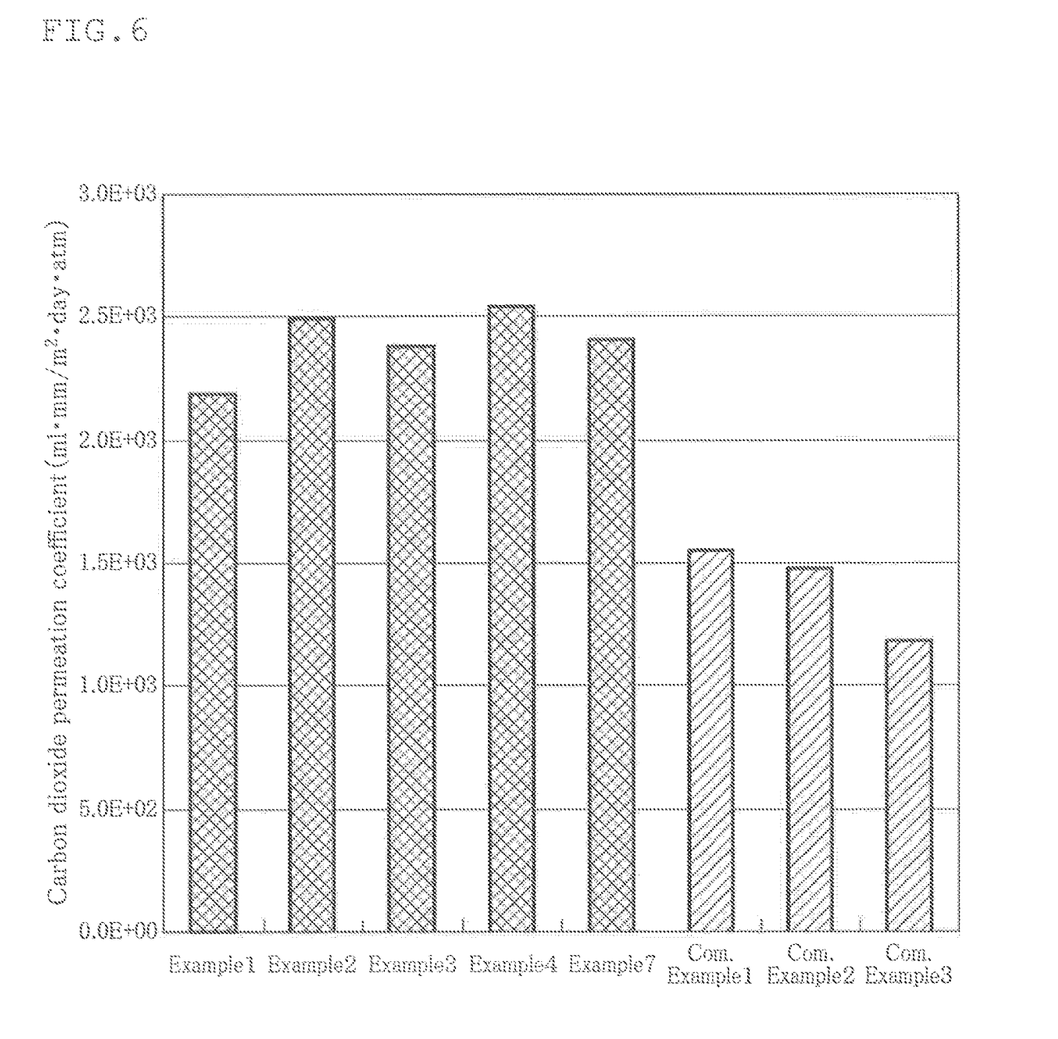
FIG. 6 is a view showing the results of measuring carbon dioxide permeation of the films of Examples and Comparative Examples.

Further, by using this cell culture film, the carbon dioxide permeability per unit thickness (ml·mm/m$^2$·day·atm (37° C.-80% RH)) was similarly measured by means of the gas permeability measuring device GPM-250. The results are shown in FIG. 6. This figure shows that, a higher carbon dioxide permeability, a higher gas permeability of the cell culture film.

As shown in the figure, the carbon dioxide permeability of the cell culture film obtained in Example 1 was about 2190 ml·mm/m$^2$·day·atm (37° C.-80% RH).

Example 2

A cell culture film composed of three layers was produced in the same manner as in Example 1. As the base material, Kernel KS340T (LLDPE, manufactured by Japan Polyethylene Corporation, density, 0.880 g/cm$^3$) was used. In the inner layer and the outer layer, a resin obtained by blending Kernel KF283 (LLDPE, manufactured by Japan Polyethylene Corporation, density, 0.921 g/cm$^3$) and Kernel KM262 (LLDPE, manufactured by Japan Polyethylene Corporation, density, 0.898 g/cm$^3$) at a weight ratio of 6:4 was used. In the cell culture film thus produced, the thickness of the base material was 63 μm, the thickness of the inner layer was 17 μm, the thickness of the outer layer was 12 μm, and the total thickness of the cell culture film was 92 μm.

By using this cell culture film, in the same manner as in Example 1, the oxygen permeability and the carbon dioxide permeability per unit thickness were measured. The results are shown in FIGS. 5 and 6.

In these figures, the oxygen permeability of the cell culture film obtained in Example 2 was about 810 ml·mm/m$^2$·day·atm (37° C.-80% RH) and the carbon dioxide permeability of the cell culture film obtained in Example 2 was about 2490 ml·mm/m$^2$·day·atm (37° C.-80% RH).

Example 3

A cell culture film composed of three layers was produced in the same manner as in Example 1. As the base material, Kernel KS240T (LLDPE, manufactured by Japan Polyethylene Corporation, density, 0.880 g/cm$^3$) was used. In the inner layer and the outer layer, EXCELLEN™ GMH CB2001 (LLDPE, manufactured by Sumitomo Chemical, density, 0.920 g/cm$^3$) was used. In the cell culture film thus produced, the thickness of the base material was 65 μm, the thickness of the inner layer was 15 μm, the thickness of the outer layer was 14 μm, and the total thickness of the cell culture film was 94 pm.

By using this cell culture film, in the same manner as in Example 1, the oxygen permeability and the carbon dioxide permeability per unit thickness were measured. The results are shown in FIGS. 5 and 6.

In these figures, the oxygen permeability of the cell culture film obtained in Example 3 was about 800 ml·mm/m$^2$·day·atm (37° C.-80% RH) and the carbon dioxide permeability of the cell culture film obtained in Example 3 was about 2380 ml·mm/m$^2$·day·atm (37° C.-80% RH).

Example 4

A cell culture film formed of two layers was subjected to co-extrusion molding by the T-die method by using a labo plastomill (manufactured by Toyo Seiki Co., Ltd.). At this time, as the base material, Kernel KS240T (LLDPE, manufactured by Japan Polyethylene Corporation, density, 0.880 g/cm$^3$) was used. As the inner layer, EXCELLEN™ GMH CB 2001 (LDPE, manufactured by Sumitomo Chemical Corporation, density, 0.920 g/cm$^3$) was used. In the cell culture film thus produced, the thickness of the base material was 88 μm, the thickness of the inner layer was 18 μm, and the total thickness of the cell culture film was 106 μm.

By using this cell culture film, in the same manner as in Example 1, the oxygen permeability and the carbon dioxide permeability per unit thickness were measured. The results are shown in FIGS. 5 and 6.

In these figures, the oxygen permeability of the cell culture film obtained in Example 4 was about 910 ml·mm/m·day·atm (37° C.-80% RH) and the carbon dioxide permeability of the cell culture film obtained in Example 4 was about 2540 ml·mm/m$^2$·day·atm (37° C.-80% RH).

Example 7

A cell culture film formed of three layers was subjected to co-extrusion molding by the T-die method by using a labo plastomill (manufactured by Toyo Seiki Co., Ltd.). At this time, as the base material, Kernel KF261T (LLDPE, manufactured by Japan Polyethylene Corporation, density, 0.898 g/cm$^3$) was used. As the inner layer, UMERIT 125FN (LLDPE, manufactured by Ube-Maruzen Polyethylene, density, 0.924 g/cm$^3$) was used and as the outer layer, UMERIT 125FN (LLDPE, manufactured by Ube-Maruzen Polyethylene, density, 0.924 g/cm$^3$) was used. In the cell culture film thus produced, the thickness of the base material was 75 μm, the thickness of the inner layer was 12 µm, the thickness of the outer layer was 13 µm, and the total thickness of the cell culture film was 100 µm.

By using this cell culture film, in the same manner as in Example 1, the oxygen permeability and the carbon dioxide permeability per unit thickness were measured. The results are shown in FIGS. 5 and 6.

In these figures, the oxygen permeability of the cell culture film obtained in Example 7 was about 780 ml·mm/m$^2$·day·atm (37° C.-80% RH) and the carbon dioxide permeability of the cell culture film obtained in Example 7 was about 2400 ml·mm/m$^2$·day·atm (37° C.-80% RH).

Comparative Example 1

A single-layer cell culture film was produced by means of a labo plastomill by using Evolue SP0511 (LLDPE, manufactured by Prime Polymer Co., Ltd, density; 0.903 g/cm$^3$). The thickness of this cell culture film was 97 µm.

By using this cell culture film, in the same manner as in Example 1, the oxygen permeability and the carbon dioxide permeability per unit thickness were measured. The results are shown in FIGS. 5 and 6.

In these figures, the oxygen permeability of the cell culture film obtained in Comparative Example 1 was about 500 ml·mm/m$^2$·day·atm (37° C.-80% RH) and the carbon dioxide permeability of the cell culture film obtained in Comparative Example 1 was about 1550 ml·mm/m$^2$·day·atm (37° C.-80% RH).

Comparative Example 2

A single-layer cell culture film was produced by using Harmorex NF325N (LLDPE, manufactured by Prime Polymer Co., Ltd, density; 0.908 g/cm$^3$). The thickness of the cell culture film was 97 µm.

By using this cell culture film, in the same manner as in Comparative Example 1, the oxygen permeability and the carbon dioxide permeability per unit thickness were measured. The results are shown in FIGS. 5 and 6.

In these figures, the oxygen permeability of the cell culture film obtained in Comparative Example 2 was about 480 ml·mm/m$^2$·day·atm (37° C.-80% RH) and the carbon dioxide permeability of the cell culture film obtained in Comparative Example 2 was about 1480 ml·mm/m$^2$·day·atm (37° C.-80% RH).

Comparative Example 3

A single-layer cell culture film was produced by using Kernel KF271 (LLDPE, manufactured by Japan Polyethylene Corporation, density, 0.913 g/cm$^3$)). The thickness of the cell culture film was 97 µm.

By using this cell culture film, in the same manner as in Comparative Example 1, the oxygen permeability and the carbon dioxide permeability per unit thickness were measured. The results are shown in FIGS. 5 and 6.

In these figures, the oxygen permeability of the cell culture film obtained in Comparative Example 3 was about 370 ml·mm/m$^2$·day·atm (37° C.-80% RH) and the carbon dioxide permeability of the cell culture film obtained in Comparative Example 3 was about 1180 ml·mm/m$^2$·day·atm (37° C.-80% RH).

From the above results, it can be understood that the oxygen permeabilities of Examples 1 to 4 and 7 were larger by 94%, 62%, 60%, 82% and 56%, respectively, than the oxygen permeability of Comparative Example 1 (the largest oxygen permeation coefficient of Comparative Examples).

Further, it can be understood that the carbon dioxide permeabilities of Examples 1 to 4 and 7 were larger by 41%, 61%, 54%, 64% and 55% than the carbon dioxide permeability of Comparative Example 1 (the largest carbon dioxide permeability of Comparative Examples).

Accordingly, it is revealed that the cell culture film and the cell culture container produced by using it exhibited excellent gas permeability.

<Cell Culture Test 1>

Example 5

Next, by using the cell culture film obtained in Example 1, two cell culture containers were produced. The cell culture test was conducted at different culture periods by using each of the culture containers.

Figure 7:
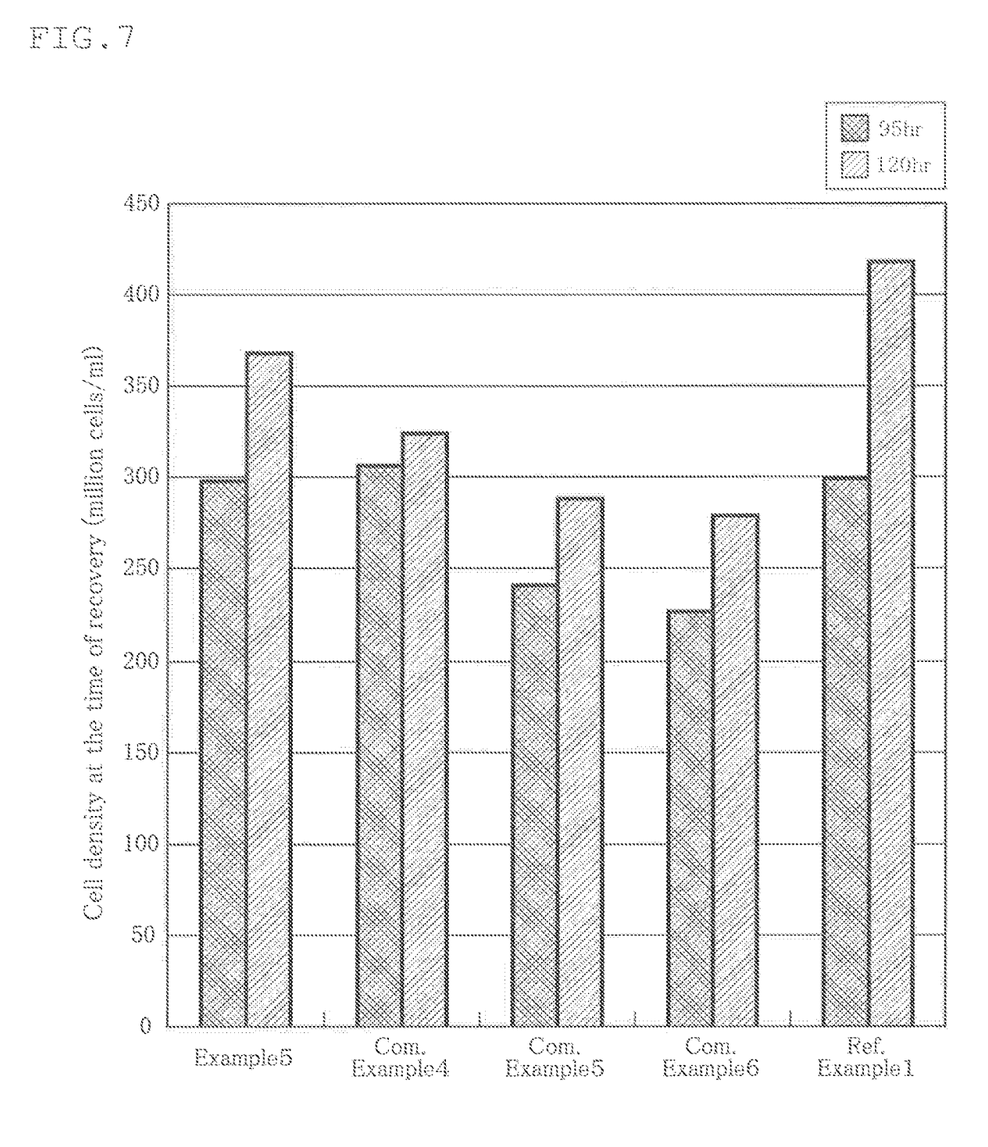
FIG. 7 is a view showing the results of the cell culture test 1 of the films of Examples and Comparative Examples.

The size of the cell culture container was 80 mm×80 mm. As the culture medium, 50 ml of AlyS505N-7 (manufactured by Cell Science & Technology Institute, Inc.) was used. As the cultivation cell, hPBMC (Human Peripheral Blood Mononuclear Cells, Cell Applications, Inc.) was used, and the initial cell density was 180000 cells/ml. The results are shown in FIG. 7.

As shown in this figure, the cell density (cells/ml) at the harvest when the culture period was 95 hours was about 2980000, and the cell density (cells/ml) at the harvest when the culture period was 120 hours was about 3700000.

Comparative Example 4

Two cell culture containers were produced by using the cell culture film of Comparative Example 1. The cell culture test was conducted at different culture periods by using each of the culture containers.

Conditions such as the size of the cell culture container, the medium, the culture cell and the initial cell density were the same as those in Example 5, and only the cell culture film forming the cell culture container was different from that in Example 5. The results are shown in FIG. 7.

As shown in this figure, the cell density (cells/ml) at the harvest when the culture period was 95 hours was about 3050000, and the cell density (cells/ml) at the harvest when the culture period was 120 hours was about 3240000.

Comparative Example 5

Two cell culture containers were produced by using the cell culture film of Comparative Example 2. The cell culture test was conducted at different culture periods by using each of the culture containers.

Conditions such as the size of the cell culture container, the culture medium, the culture cell and the initial cell density were the same as those in Example 5, and only the cell culture film forming the cell culture container was different from that in Example 5. The results are shown in FIG. 7.

As shown in this figure, the cell density (cells/ml) at the harvest when the culture period was 95 hours was about 2410000, and the cell density (cells/ml) at the harvest when the culture period was 120 hours was about 2880000.

Comparative Example 6

Two cell culture containers were produced by using the cell culture film of Comparative Example 3. The cell culture test was conducted at different culture periods by using each of the culture containers.

Conditions such as the size of the cell culture container, the culture medium, the culture cell and the initial cell density were the same as those in Example 5, and only the cell culture film forming the cell culture container was different from that in Example 5. The results are shown in FIG. 7.

As shown in this figure, the cell density (cells/ml) at the harvest when the culture period was 95 hours was about 2270000, and the cell density (cells/ml) at the harvest when the culture period was 120 hours was about 2790000.

Referential Example 1

By using two cell culture dishes (manufactured by Becton Dickinson and Company), the cell culture test was conducted at different culture periods (control test).

Conditions such as the size of the cell culture container, the culture medium, the culture cell and the initial cell density were the same as those in Example 5, and Referential Example 1 was different from Example 5 in that the cell culture was conducted in an open system without using a cell culture bag. The results are shown in FIG. 7.

As shown in this figure, the cell density (cells/imp at the harvest when the culture period was 95 hours was about 3000000, and the cell density (cells/ml) at the harvest when the culture period was 120 hours was about 4180000.

As is understood from the above results, when the culture period was 95 hours, the cell density using the cell culture container of Example 5 was almost the same as that in Comparative Example 4 in which the single-layer cell culture container was used or the open system culture shown in Reference Example 1.

However, as the culture period was prolonged, influence of the gas permeability of the cell culture bag became large. When the culture period was 120 hours, the cell density when using the cell culture container of Example 5 was increased by about 14%, 28% and 33%, respectively, as compared with the cell density when the cell culture containers shown in Comparative Examples 4 to 6 were used.

Further, when the culture period was 95 hours, the cell density when using icy the cell culture container of Example 5 was increased by about 24% and 31%, respectively, as compared with the cell density when the cell culture containers shown in Comparative Examples 5 and 6 were used.

<Cell Culture Test 2>

Example 6

Next, by using the cell culture film obtained in Example 1, two cell culture containers were produced. The cell culture test was conducted at different culture periods by using each of the culture containers.

Figure 8:
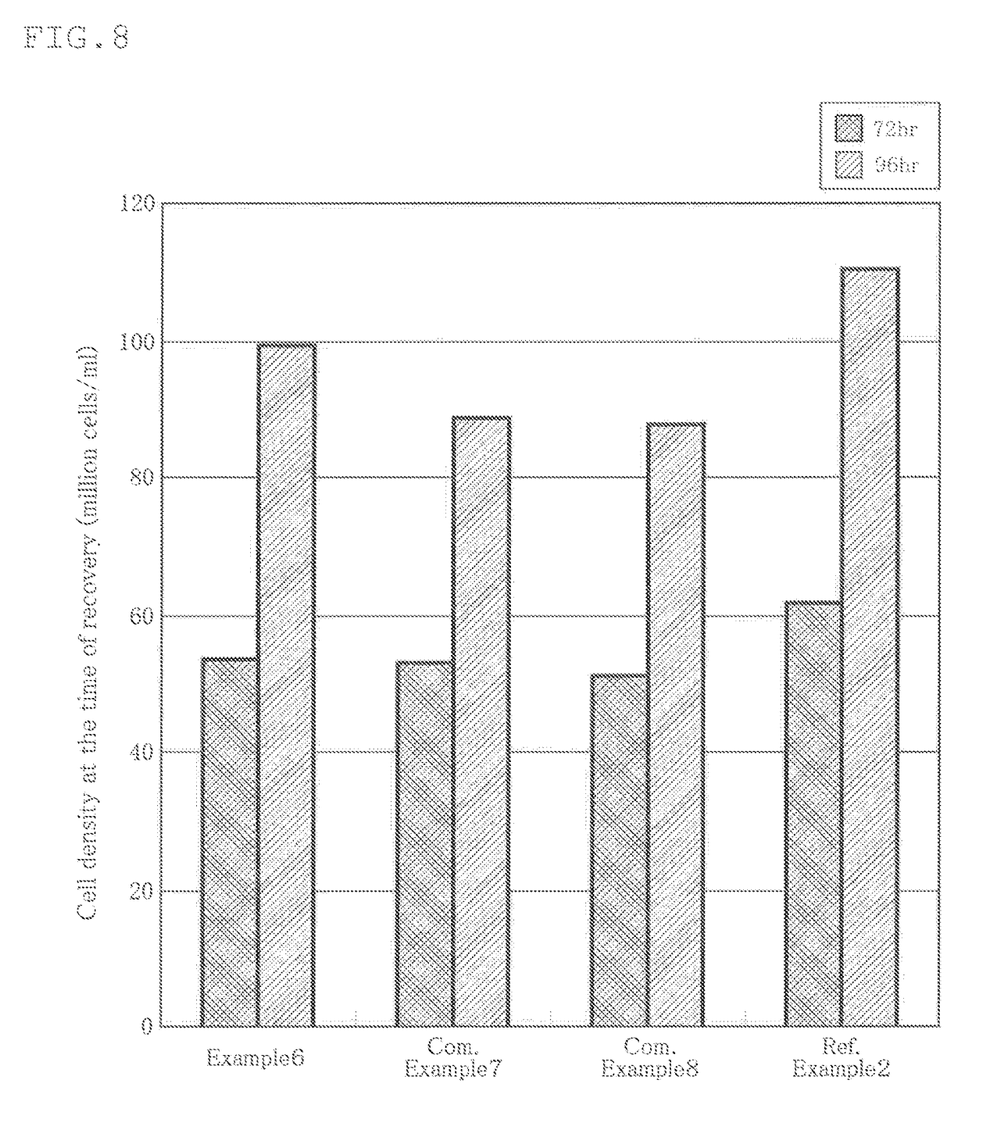
FIG. 8 is a view showing the results of the cell culture test 2 of the films of Examples and Comparative Examples.

The size of the cell culture container was 80 mm×80 mm. As the culture medium, 40 ml of AlyS505N-0 (manufactured by Cell Science & Technology Institute, Inc.) was used. As the cultivation cell, 6.1 Jurkat E (Human leukaemic T cell lymphoblast) was used, and the initial cell density was about 46000 cells/ml. The results are shown in FIG. 8.

As shown in this figure, the cell density (cells/ml) at the harvest when the culture period was 72 hours was about 530000, and the cell density (cells/ml) at the harvest when the culture period was 96 hours was about 990000.

Comparative Example 7

Next, by using the cell culture film obtained in Comparative Example 1, two cell culture containers were produced.

The cell culture test was conducted at different culture periods by using each of the culture containers.

Conditions such as the size of the cell culture container, the culture medium, the culture cell and the initial cell density were the same as those in Example 6, and only the cell culture film forming the cell culture container was different from that in Example 6. The results are shown in FIG. 8.

As shown in this figure, the cell density (cells/ml) at the harvest when the culture period was 72 hours was about 530000, and the cell density (cells/ml) at the harvest when the culture period was 96 hours was about 890000.

Comparative Example 8

By using the cell culture film obtained in Comparative Example 2, two cell culture containers were produced. The cell culture test was conducted at different culture periods by using each of the culture containers.

Conditions such as the size of the cell culture container, the culture medium, the culture cell and the initial cell density were the same as those in Example 6, and only the cell culture film forming the cell culture container was different from that in Example 6. The results are shown in FIG. 8.

As shown in this figure, the cell density (cells/ml) at the harvest when the culture period was 72 hours was about 510000, and the cell density (cells/ml) at the harvest when the culture period was 96 hours was about 880000.

Referential Example 2

By using two cell culture dishes (manufactured by Becton Dickinson and Company), the cell culture test was conducted at different culture periods (control test).

Conditions such as the size of the cell culture container, the culture medium, the culture cell and the initial cell density were the same as those in Example 6, and Referential Example 2 was different from Example 6 in that the cell culture was conducted in an open system without using a cell culture bag. The results are shown in FIG. 8, As shown in this figure, the cell density (cells/ml) at the harvest when the culture period was 72 hours was about 620000, and the cell density (cells/ml) at the harvest when the culture period was 96 hours was about 1110000.

As is understood from the above results, when the culture period was 72 hours, the cell density using the cell culture container of Example 6 was almost the same as that when the cell culture containers of Comparative Examples 7 and 8 were used, and was slightly smaller than the cell density obtained by the open-type culture in Referential Example 2.

However, as the culture period was prolonged, influence of the gas permeability of the cell culture bag became large, When the culture period was 96 hours, the culture density when using the cell culture bag of Example 6 was increased by about 11% and 13%, respectively, as compared with the cell density when the cell culture containers shown in Comparative Examples 7 and 8 were used.

As mentioned above, it was revealed that, if the conditions such as the cells to be cultivated, the cultivation medium and the initial cell density were changed, according to the cell culture container formed by using the cull culture film having a high gas permeability of the present invention, cell culture efficiency could be improved.

<Cell Culture Test 3>

Example 8

Next, by using the cell culture film obtained in Example 7, two cell culture containers were produced. The cell culture test was conducted at different culture periods by using each of the culture containers.

The size of the cell culture container was 80 mm×80 mm. As the culture medium, 40 ml of AlyS505N-7 (manufactured by Cell Science & Technology Institute, Inc.) was used.

Figure 9:
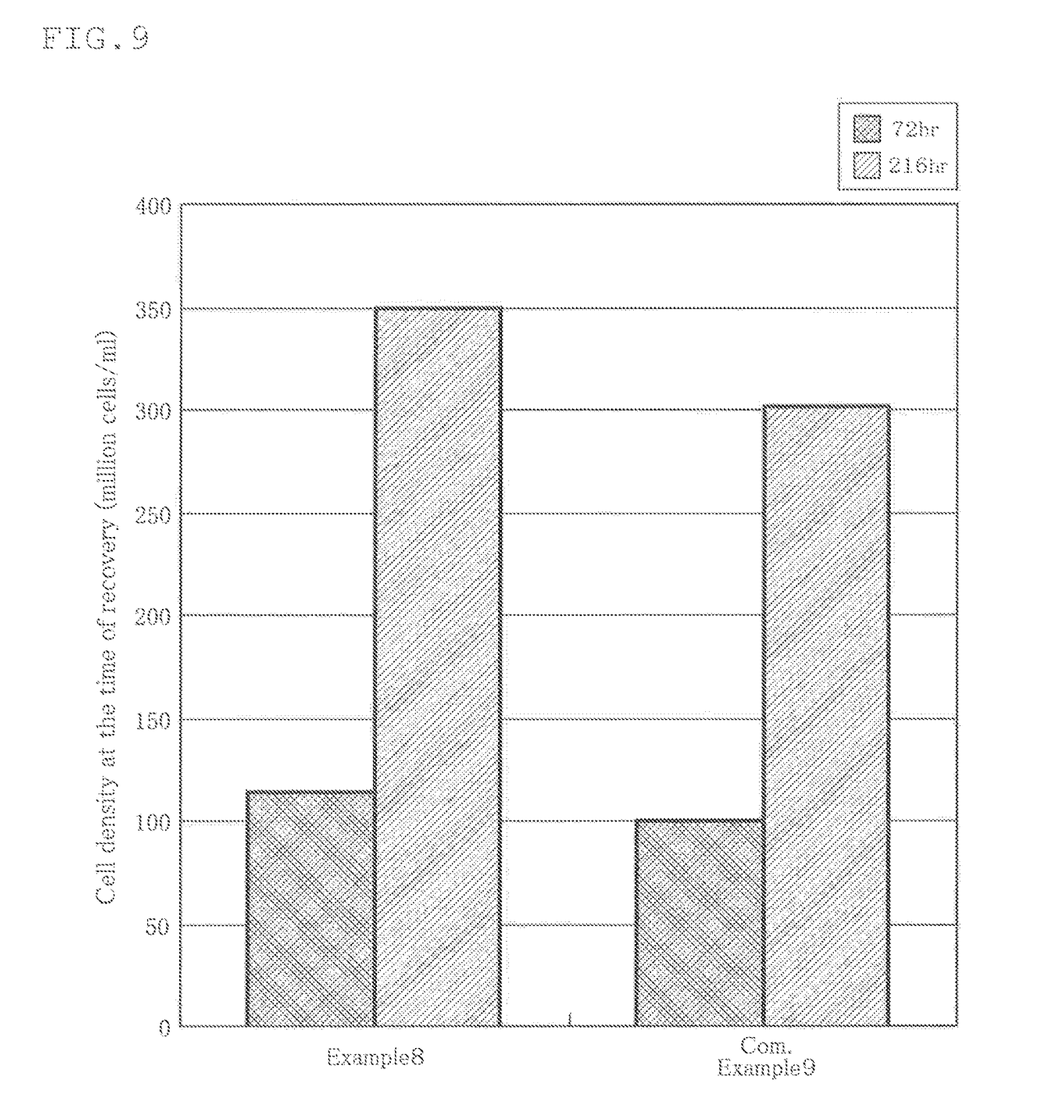
FIG. 9 is a view showing the results of the cell culture test 3 of the films of Examples and Comparative Examples.

As the cultivation cell, hPBMC (Human Peripheral Blood Mononuclear Cells, Cell Applications, Inc.) was used, and the initial cell density was 185000 cells/ml. The results are shown in FIG. 9.

As shown in this figure, the cell density (cells/ml) at the harvest when the culture period was 72 hours was about 1140000, and the cell density (cells/ml) at the harvest when the culture period was 216 hours was about 3500000.

Comparative Example 9

By using the cell culture film obtained in Comparative Example 2, two cell culture containers were produced. The cell culture test was conducted at different culture periods by using each of the culture containers.

Conditions such as the size of the cell culture container, the culture medium, the culture cell and the initial cell density were the same as those in Example 8, and only the cell culture film forming the cell culture container was different from that in Example 8. The results are shown in FIG. 9.

As shown in this figure, the cell density (cells/ml) at the harvest when the culture period was 72 hours was about 1000000, and the cell density (cells/ml) at the harvest when the culture period was 216 hours was about 3010000.

As is understood from the above results, when the culture period was 72 hours, the cell density when using the cell culture container of Example 8 was increased by about 14% as compared with the cell density when the cell culture container shown in Comparative Example 9 was used. Further, when the culture period was 216 hours, the cell density when using the cell culture container of Example 8 was increased by about 16% as compared with the cell density when icy the cell culture container shown in Comparative Example 9 was used.

It has been revealed that, when culture was conducted by using a cell culture container formed of the base material and the outer layer having a relatively high density within the range of the density of the cell culture film of the present invention, as compared with the case when culture was conducted by using a cell culture container formed of a single-layer film having a density larger than that of the base material and having a density smaller than that of the outer layer, cell culture efficiency could be improved.

The present invention is not restricted to the above-mentioned embodiments and examples, and it is needless to say that various modifications are possible within the range of the present invention.

For example, in the second embodiment, as the base material 1, a polyethylene-based resin having a density at which handling is impossible is used, and by sandwiching it between the inner layer 2 and the outer layer 3, gas permeability is further improved.

INDUSTRIAL APPLICATIBILITY

The present invention can be preferably used when cells are cultivated in a large amount by using the cell culture container.

The invention claimed is:

1. A method for culturing cells, comprising culturing cells in a cell culture container having an outer surface and an inner surface,
   wherein the cell culture container comprises a multilayer film comprising:
      an outer layer comprising a polyethylene-based resin consisting of LLDPE, LDPE or a blend thereof;
      a base material comprising a polyethylene-based resin consisting of LLDPE, ULDPE, LDPE or a blend thereof; and
      an inner layer comprising a polyethylene-based resin consisting of LLDPE, ULDPE, LDPE or a blend thereof,
   wherein the outer layer is adhered on the base material,
   wherein the inner layer forms the inner surface of the cell culture container and the outer layer forms the outer surface of the cell culture container,
   wherein a density of the outer layer is within a range of 0.886 g/cm$^3$ to 0.924 g/cm$^3$, a density of the base material is within a range of 0.87 g/cm$^3$ to 0.90 g/cm$^3$ and a density of the inner layer is within a range of 0.896 g/cm$^3$ to 0.924 g/cm$^3$, and the density of the base material is selected to be less than the density of the inner layer and the density of the outer layer, and
   wherein an oxygen permeability of the multilayer film is 750 ml·mm/m$^2$·day·atm or more as measured at 37° C. and 80%RH.

2. The method according to claim 1, wherein a thickness of the base material relative to a thickness of the multilayer film is 60% or more.

3. The method according to claim 1, wherein a carbon dioxide permeability of the multilayer film is 2100 ml·mm/m$^g$·day·atm or more as measured at 37° C. and 80%RH.

4. The method according to claim 1 wherein the inner layer forming the cell culture surface does not comprise an anti-blocking agent, a slipping agent, or a lubricant.

5. The method according to claim 1, wherein the polyethylene-base resin of the base material, the polyethylene-base resin of the inner layer and the polyethylene-base resin of the outer layer are sterilized by radiation.

6. The method according to claim 1, wherein culturing the cells is performed in a closed, gas permeable culture system, wherein the closed culture system comprises the cell culture container.

7. The method according to claim 6, wherein the cell culture container is a culture bag.

* * * * *